United States Patent [19]

Cummings et al.

[11] 3,956,415

[45] May 11, 1976

[54] PLURAL STAGE DISTILLATION WITH INTERMEDIATE INDIRECT HEAT EXCHANGE, OF FEED STREAMS COMPRISING ETHYLENE AND METHANE

[75] Inventors: Donald R. Cummings, Cheltenham, England; Kenneth J. O'Sullivan, Milson's Point, Australia

[73] Assignee: Petrocarbon Developments Limited, Manchester, England

[22] Filed: Mar. 4, 1975

[21] Appl. No.: 555,118

[30] Foreign Application Priority Data
Mar. 4, 1974 United Kingdom................. 9670/74

[52] U.S. Cl.............................. 260/683 R; 62/28; 62/31; 62/34
[51] Int. Cl.²...................... C07C 3/28; C07C 5/32; C07C 11/02
[58] Field of Search................................. 62/23–34; 260/683 R

[56] References Cited
UNITED STATES PATENTS

| | | | |
|---|---|---|---|
| 1,853,743 | 4/1932 | Pollitzer.................................. | 62/24 |
| 1,870,334 | 8/1932 | Lantz...................................... | 62/29 |
| 2,035,516 | 3/1936 | Wilkinson et al....................... | 62/26 |
| 2,180,435 | 11/1939 | Schlitt.................................... | 62/31 |
| 2,711,085 | 6/1955 | Anderson................................ | 62/30 |
| 2,817,216 | 12/1957 | Etienne................................... | 62/26 |
| 3,073,130 | 1/1963 | Becker.................................... | 62/28 |
| 3,625,017 | 12/1971 | Hoffman.................................. | 62/26 |
| 3,663,644 | 5/1972 | Harvey........................... | 260/683 R |
| 3,675,435 | 7/1972 | Jackson et al.......................... | 62/28 |

Primary Examiner—Frank W. Lutter
Assistant Examiner—Frank Sever
Attorney, Agent, or Firm—Browdy and Neimark

[57] ABSTRACT

Substantially pure methane and ethylene are supplied economically from a transportable liquefied methane-ethylene-ethane mixture by a two-stage distillation at superatmospheric pressure wherein the refrigeration for the first stage reflux may be supplied entirely from sensible cold of the compressed mixture and the second stage reflux is obtained by heat exchange with first stage reboil so that the only power requirement is for compressing the mixture. The mixture is conveniently obtained by combining a cracker gas fraction with a natural gas fraction.

19 Claims, 1 Drawing Figure

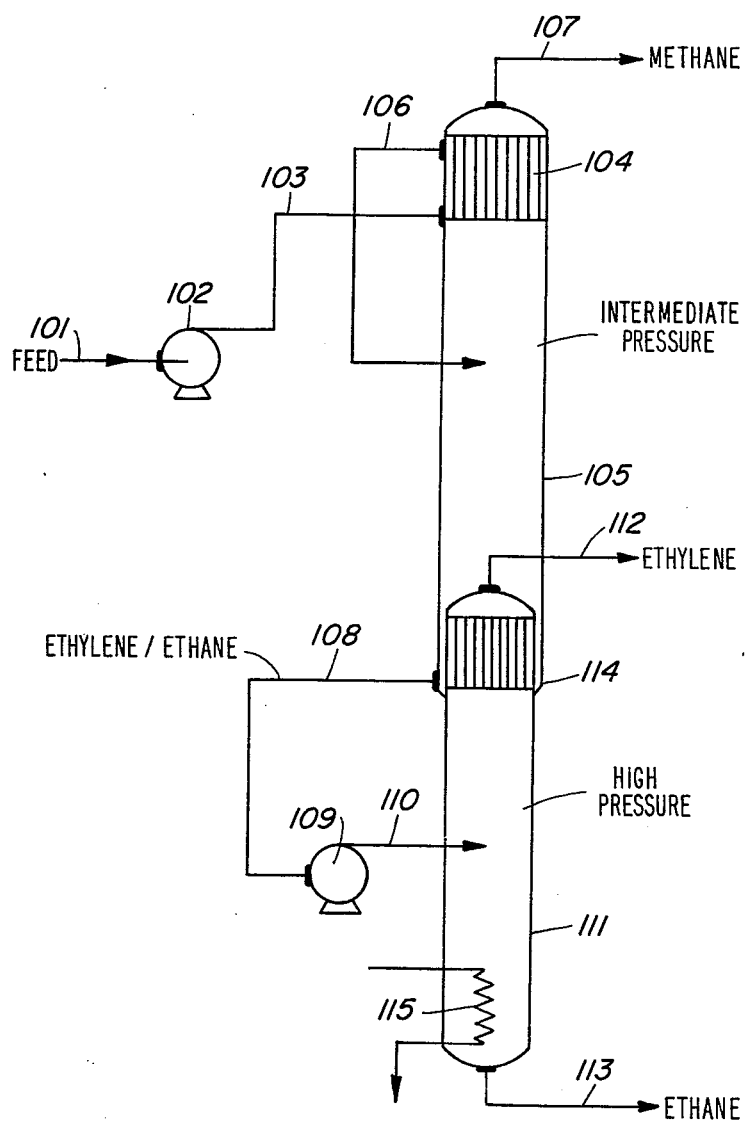

PLURAL STAGE DISTILLATION WITH INTERMEDIATE INDIRECT HEAT EXCHANGE, OF FEED STREAMS COMPRISING ETHYLENE AND METHANE

This invention relates to providing methane and ethylene and more particularly to providing these hydrocarbons in economic manner at or near their points of utilisation.

Ethylene and methane are industrial commodities for which there is a very high demand, ethylene being an important primary chemical in the production of a wide range of compounds and methane being important as a fuel.

Methane is found as the principal component of natural gas. As the sources of natural gas are generally remote from industrial locations where the methane is required as a utility, and frequently separated from them by large expanses of water, it has become commonplace to liquefy the natural gas in the vicinity of its source and transport it to the point of demand in refrigerated liquefied form in tankers specially designed for the purpose.

Ethylene is generally manufactured by the cracking of hydrocarbons and since the cracking process consumes large quantities of energy it is desirable to effect the cracking in locations where energy is cheap. Natural gas sources provide such locations and moreover natural gas generally contains appreciable amounts of hydrocarbons which can be converted to ethylene by cracking. Therefore there are valid reasons for considering the establishment of hydrocarbon cracking plants in the vicinity of natural gas sources.

However, if the ethylene were produced in such a locality, there would then be the problem of transporting it to the industrial centres where it is required as a feedstock for conversion to other chemicals.

The gas generally known as "cracker gas", which results from the cracking of a hydrocarbon stream to form ethylene, is a mixture of hydrogen and olefinic and paraffinic $C_1$–$C_4$ hydrocarbons which also contains traces of acetylene and hydrocarbons with more than four carbon atoms.

One solution that has been proposed for the problem of transporting the ethylene has been to remove from the cracker gas a heavy fraction liquefy of hydrocarbons with four or more carbon atoms, to liqquefy the remainder and to dilute the product with liquefied natural gas (LNG) so that it may be transported to the point of demand in the LNG and using existing equipment designed for the transport of LNG. As the hydrocarbon can be removed during the liquefaction, the liquid mixture which is transported will consist essentially of methane, ethylene, ethane, propylene and propane. When it reaches its destination, the methane and ethylene is intended to be recovered from the liquid mixture by low temperature distillation.

This distillation requires three distillation columns: a demethaniser which delivers methane as overhead and a mixture of $C_2$ and $C_3$ hydrocarbons as bottoms product, a de-ethaniser which delivers a $C_2$ mixture of ethylene and ethane as overhead and a mixture of propylene and propane as bottoms product, and a $C_2$-Splitter which separates the $C_2$ mixture into ethylene and ethane.

Further distillation columns may be required where extremely high ethylene purity is required or where other products, e.g. propylene, are to be obtained in the pure state.

A particular feature of this proposal is that refrigeration, to provide reflux for the distillation columns, has to be made available at several different temperatures. Thus, the reflux condenser of the demethaniser requires refrigeration around −100°C, while the de-ethaniser and the $C_2$-Splitter require reflux to be provided at temperatures in the region of −30°C, the exact temperatures depending on the pressures at which the various distillation steps are carried out.

It is usual to supply this refrigeration by means of two or more refrigerants, operated either in independent closed cycles or "in cascade," by which term is meant that a lower boiling refrigerant, such as ethylene, is liquefied at an elevated pressure in thermal contact with a higher boiling refrigerant, which may be propane, propylene or ammonia. The resulting installation is thus complex and expensive, in spite of which the thermodynamic efficiency is low, generally of the order of 10 percent, so that the power consumption is relatively high.

It would be very difficult, if indeed at all possible, for these extensive refrigeration requirements to be satisfied entirely by the evaporation and warming up to ambient temperature of the LNG in which the ethylene-containing mixture is carried, and therefore additional mechanical refrigeration would have to be provided. This is especially disadvantageous because the $C_2$-Splitter requires to be operated with a relatively high reflux ratio, and thus needs a large supply of refrigeration power, only a small portion of which is recoverable from the column reboiler.

Thus the above proposed solution will require the provision of fairly large amounts of power for gas compression at the receiving terminal which will generally be in a locality where such power will be relatively expensive.

We have now found that if the hydrocarbon portion of the liquefied material which is transported and delivered to the point of demand consists substantially entirely of methane, ethane and ethylene only, the ethylene and methane may be recovered for subsequent use at said point of demand by a cryogenic separation process whose refrigeration requirements may be satisfied entirely by the cold potential of the liquefied mixture; no further refrigeration being required. Indeed, apart from a small amount of power needed for pumping liquids, no utilities need be consumed.

According to the invention there is provided a method of supplying methane and ethylene from a mixture thereof at a location which is geographically remote from their origin, said method comprising providing at said location a compressed liquefied hydrocarbon mixture consisting essentially of methane, ethane and ethylene substantially free of $C_3$ and higher hydrocarbons, which hydrocarbon mixture has been transported in liquefied form to said location from another location which is nearer the origins of said methane and ethylene; feeding the mixture at a first superatmospheric pressure and at a temperature below its bubble point at said pressure to a first distillation column for fractionation into an overhead gaseous methane stream and a liquid bottoms fraction comprising ethylene and ethane; withdrawing a first portion of said liquid bottoms fraction from said first distillation column, increasing the pressure thereof to a higher superatmospheric pressure and feeding it at said higher superatmospheric pressure and at a temperature below its bubble point at said pressure to a second distillation column and distilling said liquid bottoms fraction in said second distillation column to provide a gaseous ethylene stream which is recovered overhead; providing the reflux for said first distillation column by condensing a portion of said gaseous methane stream and returning it to said column, the condensation being effected at least in part by indirect heat exchange between said gaseous methane stream and said liquefied mixture in a temperature range below the bubble point of said mixture and prior to feeding said mixture to said first distillation column; and providing the reflux for said second distillation column by evaporating a second portion of the liquid bottoms fraction formed in said first distillation column in indirect heat exchange with said gaseous ethylene stream whereby to condense a portion of said gaseous ethylene stream, and returning said condensed portion to said second column.

By utilising the sensible cold in the compressed mixture of methane, ethane and ethylene to provide the refrigeration for the reflux for the first distillation column, and by utilising the reboil of the liquid bottoms fraction of the first distillation column to provide the reflux for the second distillation column in the manner described, the very high reflux ratio necessary for the good separation of the ethane and ethylene in the second distillation column can be achieved without the need for additional mechanical refrigeration. However, such additional refrigeration may be used if desired.

The pressure at which the liquid mixture should be supplied to the first distillation column, which determines the degree of sub-cooling and therefore the proportion of the gaseous methane stream that can be condensed and returned as reflux to the first distillation column by indirect heat exchange with the mixture without the mixture reaching its bubble point, will depend upon the composition of the liquid mixture and on the degree of purity required in the methane and ethylene products. It can also be varied to some extent according to the pressure at which the methane product is required. In general, a pressure of from 180 to 300 psia will be suitable.

For the reflux of the second distillation column to be provided by reboil of the liquid bottoms fraction of the first distillation column, it is convenient for the first column to be superimposed on the second column with a common reboiler/condenser. Alternatively, the columns may be arranged with reflux being pumped from the sump of the first column into the reflux condenser of the second.

It is to be noted that, contrary to the arrangement normally practised in the recovery of ethylene from cracker gas, in the process of this invention the second column which is in effect the $C_2$-Splitter is operated at a higher pressure than the first column which is in effect the demethaniser. This is feasible in the process of this invention despite the resultant reduced relative volatility of ethylene to ethane because the present invention permits the second column to be operated with a high reflux ratio without the consumption of utilities.

Heat for the reboil of the liquid bottoms fraction of the second distillation column may be provided by indirect heat exchange with a fluid, suitably water, which is at ambient temperature. The cooled fluid that is recovered from the heat exchanger will provide a convenient source of sensible cold, thereby further enhancing the advantageous economics of the process.

Also, the gaseous methane and ethylene which are recovered will still be available with a significant cold potential, which may be utilised to perform other refrigerating duties at or near the receiving terminal, as may be required.

The hydrocarbon mixture which is to be provided in liquefied form in the method of the invention may be obtained by combining (a) a substantially acetylene-free $C_{1-2}$ hydrocarbon composition derived from cracker gas with (b) a hydrocarbon composition which is substantially free of $C_3$ and higher hydrocarbons and which is derived from natural gas. The invention thus permits the separation of $C_3$ and higher hydrocarbons from cracker gas at a locality where the energy for the separation may be supplied relatively cheaply, and the subsequent transfer of the ethylene in the acetylene-free $C_{1-2}$ hydrocarbon stream to any distant point of demand in solution in the natural gas from which $C_3$ and higher hydrocarbons have been removed, thereby simplifying transport by allowing the use of standard LNG tankers.

In general, natural gas consists primarily of methane and small amounts of ethane and propane. There may also be traces of higher hydrocarbons and in some natural gases nitrogen is found.

A hydrocarbon fraction consisting essentially of hydrocarbons having more than one carbon atom (i.e. essentially ethane and propane) may be readily removed from the natural gas by simple distillation at low temperatures in known manner. The remaining fraction will consist essentially of methane but nitrogen will also be present in those cases where it is found in the natural gas itself. This fraction, which is substantially free of both $C_2$ and $C_3$ hydrocarbons, may conveniently be mixed with the acetylene-free $C_{1-2}$ hydrocarbon stream derived from the cracker gas to form the feed for the process of the present invention.

The cracker gas from which the acetylene-free $C_{1-2}$ hydrocarbon stream is conveniently obtained is most desirably produced by cracking mixture of ethane and propane and accordingly the cracker gas may advantageously be prepared by cracking the ethane/propane mixture derived by distillation of the natural gas as described above. Thus, all the components for the mixture required in liquefied sub-cooled form by the present invention may advantageously be derived from natural gas by first distilling the natural gas to provide a first stream containing methane and a second stream consisting essentially of $C_2$ and higher hydrocarbons and then cracking said second stream to form the cracker gas from which the acetylene-free $C_{1-2}$ hydrocarbon stream may be derived.

As has been indicated above, cracker gas resulting from the cracking of hydrocarbons, and particularly ethane and propane, to form ethylene, generally comprises a mixture of hydrogen and olefinic and paraffinic $C_{1-4}$ hydrocarbons together with traces of acetylene and hydrocarbons having more than four carbon atoms.

Any traces of acetylene present in the cracker gas may be removed in known manner by catalytic hydrogenation and the $C_3$ and heavier hydrocarbons may then be separated from the $C_1$ and $C_2$ hydrocarbons (i.e. methane, ethane and ethylene) without difficulty in a single distillation column, using, for example, liquefied natural gas to provide reflux. The distillation may be carried out at the location where the cracker gas is produced and therefore the energy requirements may be provided relatively cheaply.

The distillation can be operated without difficulty to produce a distillate which is substantially free of $C_3$ and higher hydrocarbons and therefore consists almost entirely of hydrogen, methane, ethane and ethylene. This distillate may then be diluted with the methane from the natural gas and the product mixture liquefied. Alternatively, the distillate and the natural gas fraction may be liquefied separately and then combined. Any hydrogen which is present in the distillate may conveniently be removed at the liquefaction stage.

The liquefied mixture produced in this manner is thus substantially entirely methane, ethane and ethylene. Nitrogen may also be present if it is present in the natural gas stream, in which case it will be separated with the methane as the overhead product of the first distillation column in the process of the invention.

The mixture of methane, ethane and ethylene, optionally with some nitrogen, is transported in refrigerated liquefied form to the point of demand where it may be stored until required.

There may thus be provided at a point of demand remote from the locality of the source of natural gas or cracker gas a liquid sub-cooled mixture consisting essentially of methane, ethane and ethylene, substantially free of $C_3$ and higher hydrocarbons.

In accordance with the invention, the liquefied mixture of methane, ethane, ethylene and possibly some nitrogen is subjected to a two-stage distillation process to recover gaseous methane and ethylene in substantially pure form.

Provided that the hydrocarbon content of the mixture contains at least 75 mole % methane the cold requirements for the separation process of the invention can be met entirely from the sensible and latent cold in the compressed mixture. Mixtures containing less methane, e.g. down to 60 mole % or even lower, can be separated by the process of the invention but supplementary refrigeration may be required to provide the necessary reflux to the first distillation column. The preferred concentration of methane in the mixture is 75 to 85 mole % although larger amounts e.g. to 95 mole % acceptable.

The concentrations of ethylene and ethane in the mixture will depend upon their source. In general cracker gas contains them in a ratio in the range approximately 2:1 to 5:1. However, some ethane may also be present in the natural gas fraction with which the cracker gas fraction is preferably combined. In general, the ratio of ethylene and ethane will be in the range 1:1 to 5:1. This ratio is not critical from a process viewpoint. Although a change in the ratio changes the reflux requirement in the second column in one sense it also changes the total amount of reflux required per unit or feed mixture by approximately the same amount in the opposite sense.

As indicated above, the mixture may also contain nitrogen. The nitrogen may replace a few per cent, e.g. up to 5 mole % of the methane in the mixture.

The two-stage distillation process is carried out in two distillation columns. In the first which is in effect a demethaniser, gaseos methane is recovered overhead and the liquid bottoms fraction, which is essentially ethylene and ethane with a very small proportion of methane, is withdrawn and fed to the second column which operates at a higher pressure and temperature than the first and which is in effect a $C_2$-Splitter. Gaseous ethylene with the remaining trace of methane is recovered overhead from the second column, leaving a liquid bottoms fraction consisting mainly of ethane.

The two columns are arranged such that the refrigeration requirement for the reflux of the second column is provided by the reboil of the liquid bottoms fraction of the first column. Reboil of the liquid bottoms fraction in the second column may be effected by indirect heat exchange with water at ambient temperature.

The refrigeration requirement for the reflux of the first column is preferably provided entirely from sensible cold in the liquefied mixture, this mixture suitably being passed as coolant through the reflux condenser of the first column prior to being fed into the first column for distillation; and it will be understood that the degree of purity of the methane stream will depend upon the reflux ratio which in turn will depend upon the amount of cold available in the liquefied mixture. The amount of cold in the liquefied mixture depends upon the composition of the mixture and the degree to which it is sub-cooled.

The liquefied mixture will normally be provided from the storage tanks, or the tanker vessel in which it has been shipped, at about its bubble temperature and at about or slightly above atmospheric pressure. Therefore, to provide the required degree of sub-cooling of the liquefied mixture so that it may provide the refrigeration requirements for the desired reflux of the first column and still be recovered from the reflux condenser in liquid sub-cooled form for subsequent feeding to the first distillation column, it will generally be necessary to compress the liquefied mixture to a suitable pressure prior to feeding it to the reflux condenser.

The second column must be operated at a higher pressure than the first column, since the pure ethylene leaving the top of the second column has to be condensed in thermal contact with the ethylene-ethane mixture in the base of the first column. Therefore the liquid bottoms fraction recovered from the first column, which is at its bubble-point at the operating pressure of this column, is compressed further to the operating pressure of the second column.

Thus, in one embodiment the liquefied mixture is compressed, passed as coolant through the reflux condenser of the first column and thereafter fed to an intermediate point of the first column for fractionation into a gaseous methane stream recovered overhead and a liquid bottoms fraction consisting essentially of ethylene, ethane and a very small amount of methane, and the liquid bottoms fraction is recovered, compressed to a higher pressure and fed to an intermediate point of the second column where it is fractionated into a gaseous ethylene stream recovered overhead and a liquid bottoms fraction consisting essentially of ethane.

The operating pressure of the first column is fixed primarily by the degree of sub-cooling required in the feed mixture to provide the refrigeration for the reflux of the first column and this in turn depends upon the composition of the mixture, the temperature at which it is supplied and the degree of purity required in the methane stream. However, in general, the pressure will be in the range 180 to 300 psia (assuming negligable pressure drop through the reflux condenser of the first column). For compositions containing the much preferred range of 75 to 85 mole % methane supplied at about their bubble temperature at atmospheric pressure, the operating pressure of the first column will generally be in the range 225 to 265 psia (again assuming negligable pressure drop through the reflux condenser of the first column).

The operating temperature of the first column will depend upon the operating pressure but will generally be in the range 150°K to 170°K and is preferably in the range 160°K to 165°K at the top and from 230°K to 260°K, preferably 240°K to 250°K at the bottom.

The reflux ratio operated in the first column will depend upon the degree of purity desired in the methane product stream. In general, reflux ratios of from 0.3 to 0.5 are preferred. At lower reflux ratios, the degree of purity of the methane stream may be insufficient for some purposes and at a higher ratios, the refrigeration demands will become difficult to attain.

The operating pressure of the second column will depend upon that of the first. In general, the second column pressure will be from 70 to 100 psi higher than that of the first column, with preferred pressures from 80 to 90 psi higher than that of the first column.

The operating temperature of the second column will follow from the operating pressure and will in general be in the range 230°K to 270°K, preferably 240°K to 255°K at the top and from 250°K to 280°K, preferably 265°K to 275°K at the bottom.

The reflux ratio operated in the second column will depend upon the degree of purity desired in the ethylene product stream. Because of the high operating pressure of the column, relatively high reflux ratios are desired but it is a feature of this invention that such ratios can be attained without mechanical refrigeration. In general, the reflux ratio will be in the range 5 to 8. At lower reflux ratios, the ethylene may not be sufficiently pure for some purposes and higher reflux ratios will be difficult to achieve. Preferred reflux ratios will be in the range 6 to 7. The required reflux ratio will be obtained by adjusting the amount of liquid bottoms product that is reboiled.

The invention is now illustrated by the following Example.

The first part of this Example illustrates one way of obtaining the compressed liquefied hydrocarbon mixture which is transported to the point of demand for subsequent treatment to separate and recover the methane and ethylene.

A stream of natural gas at about 50 atmospheres and having the following approximate hydrocarbon composition:

|  | Mole % |
|---|---|
| Methane $CH_4$ | 92 |
| Ethane $C_2H_6$ | 6 |
| Propane $C_3H_8$ | 2 |
|  | 100 | is taken from a well, freed of moisture, treated in known manner to remove $H_2S$ and $CO_2$, and thereafter expanded to a lower superatmospheric pressure, e.g. 35 atmospheres and cooled to a suitable low temperature e.g. about −90°C, for fractionation to separate the methane from the heavier hydrocarbons.

The fractionation is carried out in a demethaniser column in which the reflux may be provided by liquefied natural gas. Methane and some nitrogen are withdrawn overhead and $C_2$ and higher hydrocarbons are withdrawn as bottoms product. The overhead can be passed in indirect heat exchange with the incoming natural gas to assist cooling the latter.

A bottoms product with the following approximate composition is obtained:

|  | Mole % | Mols | (per 100 mols of natural gas fed to the column) |
|---|---|---|---|
| $C_2H_6$ | 75 | 6 | |
| $C_3H_8$ | 25 | 2 | |
|  | 100 | 8 | |

This bottoms product is then warmed, suitably in indirect heat exchange with the incoming natural gas to assist cooling the latter, expanded to low pressure and fed to a cracker from which a cracker gas having the following approximate composition is typically obtained:

|  | Mole % | Mols | (per 8 mols of bottoms product) |
|---|---|---|---|
| $H_2$ | 30.4 | 4.1 | |
| $CH_4$ | 13.3 | 1.8 | |
| $C_2H_4$ | 33.3 | 4.5 | |
| $C_2H_6$ | 15.6 | 2.1 | |
| $C_3H_6$ | 7.4 | 1.0 | |
|  | 100.0 | 13.5 | |

The cracker gas will also contain a few tenths of one per cent of acetylene and traces of $C_4$ and heavier hydrocarbons.

This cracker gas is quenched and cooled in known manner, compressed to about 30 atmospheres and dried. It is then treated to remove catalytically the traces of acetylene, again in known manner.

The resultant mixture is then cooled to about −100°C at about 30–35 atmospheres absolute. This may be effected, for example, in two exchangers, the second of which is a refluxing exchanger, with a separator following each exchanger. With the mixture cooled to about −40°C in the first exchanger, substantially all the $C_3$ hydrocarbon in the mixture is recovered in the liquid collected in the first separator. This liquid is then fed to a distillation column to recover any $C_1$ and $C_2$ hydrocarbons that have condensed out with the $C_3$ hydrocarbon in the first heat exchanger. Reflux for the distillation column may be provided by liquefied natural gas. In the second separator, a liquid consisting substantially only of $CH_4$, $C_2H_4$ and $C_2H_6$, is separated from the non-condensibles, such as hydrogen. This liquid is then evaported by passing it back through the second exchanger and is added to the overhead from the distillation column. The resultant gas stream has the following approximate composition:

|  | Mol % | Mols | (per 13.5 mols of cracker gas) |
|---|---|---|---|
| $CH_4$ | 21.4 | 1.8 | |
| $C_2H_4$ | 53.6 | 4.5 | |
| $C_2H_6$ | 25.0 | 2.1 | |
|  | 100.0 | 8.4 | |

This stream is then cooled and liquefied to produce a first liquefied stream and the overhead stream from the demethaniser column is also cooled and liquefied, whereby to produce separately a second liquefied stream.

The first liquefied stream is then mixed with sufficient of the second liquefied stream to obtain a liquefied mixture of the following composition:

|     | Mol % | Mols |
| --- | --- | --- |
| CH₄ | 79.0 | 24.8 |
| C₂H₄ | 14.3 | 4.5 |
| C₂H₆ | 6.7 | 2.1 |
|     | 100.0 | 31.4 |

The mixture contains 79% methane and 21% C$_2$ hydrocarbons.

This liquefied mixture is transported in a tanker ship to the point of demand for the ethylene and methane where it is supplied at its bubble point of 116°K at atmospheric pressure.

The schematic drawing shows a preferred embodiment of the invention.

The separation of the liquefied mixture into methane and ethylene will now be described with the aid of the accompanying drawing, which is a schematic flow sheet of one method of recovering the ethylene and methane from the liquefied mixture in accordance with the invention.

The liquid stream is supplied through pipeline 101, pumped to 17 atmospheres (250 psia), at which its bubble point is 167°K, in pump 102 and then passed through line 103 at about 116°K to the reflux condenser 104 of the column 105 as collant for the reflux condenser.

Leaving the reflux condenser at about 156°K, still in liquid sub-cooled form, the liquid is conveyed through the line 106 to an intermediate tray of the column 105. In this column, which has 11 theoretical plates, it is separated into substantially pure gaseous methane overhead, which is withdrawn through line 107 at about 160°K, and at the rate of about 79–80 moles per 100 mols of feed, and a liquid bottoms fraction constituting the remaining 20 – 21 mols per 100 mols of feed and consisting of a mixture of ethylene and ethane and having the following approximate composition:

|     | Mol % |
| --- | --- |
| C₂H₄ | 68 |
| C₂H₆ | 32 |
|     | 100 |

This liquid mixture, which is at about its bubble point of 243°K at 17 atmospheres, is conveyed through line 108 to the pump 109, in which the pressure is raised further to 23 Atma at which its bubble point is 272°K. The liquid, which is not at 248°K which is below its bubble point, is fed through line 110 to an intermediate tray of the second column 110 which has 49 theoretical plates. Here it is separated into a substantially pure gaseous ethylene overhead and a liquid bottoms product consisting of almost pure ethane. The ethylene product leaves through the line 112 at about 249°K and at a rate of about 14.4 mols per 100 of feed and the ethane leaves through the line 113 at about 270°K.

The reflux condenser 114 of the second column is combined with the re-boiler of the first column whereby refrigeration for the reflux of the second column is provided by first column liquid bottoms fraction reboil. Boil-up for the second column is provided by cooling water, which enters the reboiler 15 at about 20°C and leaves it at about 5°C.

The reflux ratio in the first column is about 0.5 and that in the second column is about 6.5.

The flow of cooling water is about 40 tonnes per tonne of ethylene product.

The estimated power consumed by the two pumps 102, 109 is approximately 60 kWh per tonne of ethylene produced.

We claim:

1. A method of supplying methane and ethylene from a mixture thereof at a location which is geographically remote from the origins of said methane and ethylene, said method comprising the steps of:

transporting a volume of a liquefied hydrocarbon mixture consisting essentially of methane, ethane and ethylene to said location from another location which is nearer the origins of said methane and ethylene;

compressing the mixture to a first superatmospheric pressure;

feeding the mixture at said first superatmospheric pressure and at a temperature below its bubble point at said pressure to a first distillation column and fractionating the mixture into an overhead gaseous methane stream and a liquid bottoms fraction comprising ethylene and ethane;

withdrawing a first portion of said liquid bottoms fraction from said first distillation column, increasing the pressure thereof to a second superatmospheric pressure which is above said first superatmospheric pressure and feeding it at said second superatmospheric pressure and at a temperature below its bubble point at said second pressure to a second distillation column and distilling said liquid bottoms fraction in said second distillation column to provide a gaseous ethylene stream which is recovered overhead;

producing the reflux for said first distillation column by condensing a portion of said gaseous methane stream and returning it to said first column, the condensation being effected substantially entirely by indirect heat exchange between said gaseous methane stream and said compressed liquefied hydrocarbon mixture in a temperature range below the bubble point of said mixture and prior to feeding said mixture to said first distillation column; and producing the reflux for said second distillation column by evaporating a second portion of the liquid bottoms fraction formed in said first distillation column in indirect heat exchange with said gaseous ethylene stream whereby to condense a portion of said gaseous ethylene stream, and returning said condensed portion to said second column, the evaporated second portion of the liquid bottoms fraction constituting re-boil for said first distillation column.

2. A method as claimed in claim 1 wherein said hydrocarbon mixture contains at least 75 mol percent methane and said condensation of said portion of said gaseous methane stream is effected wholly by indirect heat exchange with said liquefied mixture.

3. A method as claimed in claim 1 wherein said first superatmospheric pressure is a pressure of from 180 to 300 psia.

4. A method as claimed in claim 1 in which reboil of the liquid bottoms fraction of the second distillation column is effected by indirect heat exchange with a fluid at ambient temperature.

5. A method as claimed in claim 1 wherein said hydrocarbon mixture is a mixture of (a) a substantially acetylene-free C$_{1-2}$ hydrocarbon composition derived from cracker gas and (b) a hydrocarbon composition which is substantially free of $C_3$ and higher hydrocarbons and which is derived from natural gas.

6. A method as claimed in claim 5 in which said first-mentioned hydrocarbon composition has been obtained by cracking a natural gas fraction consisting predominantly of ethane and propane.

7. A method as claimed in claim 5 in which said hydrocarbon mixture has been obtained by distilling natural gas to provide a first stream containing methane and a second stream consisting essentially of $C_2$ and higher hydrocarbons, cracking said second stream to form a cracker gas, deriving a substantially acetylene-free $C_{1-2}$ hydrocarbon stream from said cracker gas and combining at least a portion of said acetylene-free hydrocarbon stream with at least a portion of said first stream.

8. A method as claimed in claim 1 wherein said hydrocarbon mixture contains 75 to 85 mol percent methane.

9. A method as claimed in claim 8 wherein said first superatmospheric pressure is in the range 225 to 265 psia.

10. A method as claimed in claim 1 wherein the temperature at the top of said first distillation column is in the range 150° to 170°K and at the bottom is in the range 230° to 260°K.

11. A method as claimed in claim 10 in which the temperature at the top of said column is in the range 160° to 165°K and at the bottom of said column is in the range 240° to 250°K.

12. A method as claimed in claim 1 in which the reflux ratio of said first distillation column is from 0.3 to 0.5.

13. A method as claimed in claim 1 in which said second superatmospheric pressure is 70 to 100 psi greater than said first superatmospheric pressure.

14. A method as claimed in claim 13 wherein said second superatmospheric pressure is 80 to 90 psi higher than said first superatmospheric pressure.

15. A method as claimed in claim 1 wherein the temperature at the top of said second distillation column is in the range 230° to 270°K and at the bottom of said column is in the range 250° to 280°K.

16. A method as claimed in claim 15 in which the temperature at the top of said second distillation column is in the range 240° to 255°K and at the bottom of said column is in the range 265° to 275°K.

17. A method as claimed in claim 1 wherein the reflux ratio in the second distillation column is from 5 to 8.

18. A method as claimed in claim 17 wherein said reflux ratio is from 6 to 7.

19. A method as claimed in claim 1 in which the ratio of ethylene to ethane in the hydrocarbon mixture is from 1:1 to 5:1.

* * * * *

UNITED STATES PATENT AND TRADEMARK OFFICE
CERTIFICATE OF CORRECTION

PATENT NO. : 3,956,415

DATED : May 11, 1976

INVENTOR(S) : Donald R. Cummings et al

It is certified that error appears in the above-identified patent and that said Letters Patent are hereby corrected as shown below:

Column 1, line 47, change "liquefy" to --consisting--

Column 1, line 48, change "liqquefy" to --liquefy--

Column 1, lines 52-53, "hydrocarbon" should read --hydrogen--

Column 9, line 49, "not" should read --now--

Signed and Sealed this

Twelfth Day of October 1976

[SEAL]

Attest:

RUTH C. MASON
Attesting Officer

C. MARSHALL DANN
Commissioner of Patents and Trademarks